US012796955B2

(12) United States Patent
Fernkvist et al.

(10) Patent No.: US 12,796,955 B2
(45) Date of Patent: Nov. 17, 2026

(54) SYSTEMS AND METHODS FOR MONITORING RESPIRATORY GASES

(71) Applicant: Masimo Corporation, Irvine, CA (US)

(72) Inventors: Per Fernkvist, Sollentuna (SE); Hithesh Kumar Gatty, Uppsala (SE)

(73) Assignee: Masimo Corporation, Irvine, CA (US)

( * ) Notice: Subject to any disclaimer, the term of this patent is extended or adjusted under 35 U.S.C. 154(b) by 248 days.

(21) Appl. No.: 18/598,992

(22) Filed: Mar. 7, 2024

(65) Prior Publication Data

US 2024/0298920 A1 Sep. 12, 2024

Related U.S. Application Data

(60) Provisional application No. 63/489,145, filed on Mar. 8, 2023.

(51) Int. Cl.
*A61B 5/08* (2006.01)
*A61B 5/00* (2006.01)
(Continued)

(52) U.S. Cl.
CPC .............. *A61B 5/082* (2013.01); *A61B 5/087* (2013.01); *A61B 5/097* (2013.01); *A61B 5/743* (2013.01); *G01N 33/497* (2013.01); *A61B 2560/0462* (2013.01); *G01N 33/4975* (2024.05); *G01N 2800/122* (2013.01); *G01N 2800/127* (2013.01)

(58) Field of Classification Search
None
See application file for complete search history.

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

CN 110 522 450 12/2019
CN 112 754 532 5/2021
(Continued)

OTHER PUBLICATIONS

US 2024/0016391 A1, 01/2024, Lapotko et al. (withdrawn)
(Continued)

*Primary Examiner* — Jay B Shah
(74) *Attorney, Agent, or Firm* — Knobbe, Martens, Olson & Bear LLP

(57) ABSTRACT

A device configured for monitoring a concentration of at least one volatile breathing compound. The device can include a gas interface having a mouthpiece to blow into. A connector can couple the interface to a conduit connected to a flow meter and a valve. The flow meter can measure a predefined first flux level of a patient respiratory gas flux. The gas conduit can also connect to an inlet into an intermediate gas storage. The intermediate gas storage can let patient respiratory gas exhaust in response to the flow meter sensing an expiration of the patient respiratory gas flux. A pump can draw the patient respiratory gas with a predefined second flux level in a reverse direction out of a sampling gas outlet and into a gas sampling line where exhaled concentrations of volatile breathing compound are by a detector.

20 Claims, 4 Drawing Sheets

(51) Int. Cl.

| | |
|---|---|
| *A61B 5/087* | (2006.01) |
| *A61B 5/097* | (2006.01) |
| *G01N 33/497* | (2006.01) |

(56) References Cited

U.S. PATENT DOCUMENTS 5,319,355 A 6/1994 Russek
5,337,744 A 8/1994 Branigan
5,341,805 A 8/1994 Stavridi et al.
5,377,676 A 1/1995 Vari et al.
5,431,170 A 7/1995 Mathews
5,436,499 A 7/1995 Namavar et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin, IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker

(56) References Cited

U.S. PATENT DOCUMENTS

| | | | |
|---|---|---|---|
| RE41,333 | E | 5/2010 | Blank et al. |
| 7,729,733 | B2 | 6/2010 | Al-Ali et al. |
| 7,761,127 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| RE41,912 | E | 11/2010 | Parker |
| 7,880,626 | B2 | 2/2011 | Al-Ali et al. |
| 7,909,772 | B2 | 3/2011 | Popov et al. |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,941,199 | B2 | 5/2011 | Kiani |
| 7,957,780 | B2 | 6/2011 | Lamego et al. |
| 7,962,188 | B2 | 6/2011 | Kiani et al. |
| 7,976,472 | B2 | 7/2011 | Kiani |
| 7,990,382 | B2 | 8/2011 | Kiani |
| 8,008,088 | B2 | 8/2011 | Bellott et al. |
| RE42,753 | E | 9/2011 | Kiani-Azarbayjany et al. |
| 8,028,701 | B2 | 10/2011 | Al-Ali et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,130,105 | B2 | 3/2012 | Al-Ali et al. |
| 8,182,443 | B1 | 5/2012 | Kiani |
| 8,190,223 | B2 | 5/2012 | Al-Ali et al. |
| 8,203,438 | B2 | 6/2012 | Kiani et al. |
| 8,203,704 | B2 | 6/2012 | Merritt et al. |
| 8,219,172 | B2 | 7/2012 | Schurman et al. |
| 8,224,411 | B2 | 7/2012 | Al-Ali et al. |
| 8,229,532 | B2 | 7/2012 | Davis |
| 8,233,955 | B2 | 7/2012 | Al-Ali et al. |
| 8,255,026 | B1 | 8/2012 | Al-Ali |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,315,683 | B2 | 11/2012 | Al-Ali et al. |
| RE43,860 | E | 12/2012 | Parker |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,374,665 | B2 | 2/2013 | Lamego |
| 8,388,353 | B2 | 3/2013 | Kiani et al. |
| 8,401,602 | B2 | 3/2013 | Kiani |
| 8,414,499 | B2 | 4/2013 | Al-Ali et al. |
| 8,418,524 | B2 | 4/2013 | Al-Ali |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,707 | B2 | 6/2013 | Kiani |
| 8,471,713 | B2 | 6/2013 | Poeze et al. |
| 8,473,020 | B2 | 6/2013 | Kiani et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| D692,145 | S | 10/2013 | Al-Ali et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,584,345 | B2 | 11/2013 | Al-Ali et al. |
| 8,588,880 | B2 | 11/2013 | Abdul-Hafiz et al. |
| 8,630,691 | B2 | 1/2014 | Lamego et al. |
| 8,641,631 | B2 | 2/2014 | Sierra et al. |
| 8,652,060 | B2 | 2/2014 | Al-Ali |
| 8,666,468 | B1 | 3/2014 | Al-Ali |
| 8,670,811 | B2 | 3/2014 | O'Reilly |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,702,627 | B2 | 4/2014 | Telfort et al. |
| 8,712,494 | B1 | 4/2014 | MacNeish, III et al. |
| 8,715,206 | B2 | 5/2014 | Telfort et al. |
| 8,723,677 | B1 | 5/2014 | Kiani |
| 8,740,792 | B1 | 6/2014 | Kiani et al. |
| 8,755,535 | B2 | 6/2014 | Telfort et al. |
| 8,755,872 | B1 | 6/2014 | Marinow |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,781,544 | B2 | 7/2014 | Al-Ali et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,840,549 | B2 | 9/2014 | Al-Ali et al. |
| 8,852,094 | B2 | 10/2014 | Al-Ali et al. |
| 8,852,994 | B2 | 10/2014 | Wojtczuk et al. |
| 8,897,847 | B2 | 11/2014 | Al-Ali |
| 8,911,377 | B2 | 12/2014 | Al-Ali |
| 8,989,831 | B2 | 3/2015 | Al-Ali et al. |
| 8,998,809 | B2 | 4/2015 | Kiani |
| 9,066,666 | B2 | 6/2015 | Kiani |
| 9,066,680 | B1 | 6/2015 | Al-Ali et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,131,881 | B2 | 9/2015 | Diab et al. |
| 9,138,180 | B1 | 9/2015 | Coverston et al. |
| 9,153,112 | B1 | 10/2015 | Kiani et al. |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,095 | B1 | 12/2015 | Al-Ali |
| 9,218,454 | B2 | 12/2015 | Kiani et al. |
| 9,245,668 | B1 | 1/2016 | Vo et al. |
| 9,267,572 | B2 | 2/2016 | Barker et al. |
| 9,277,880 | B2 | 3/2016 | Poeze et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,392,945 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,474,474 | B2 | 10/2016 | Lamego et al. |
| 9,480,435 | B2 | 11/2016 | Olsen |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,560,996 | B2 | 2/2017 | Kiani |
| 9,579,039 | B2 | 2/2017 | Jansen et al. |
| 9,622,692 | B2 | 4/2017 | Lamego et al. |
| D788,312 | S | 5/2017 | Al-Ali et al. |
| 9,649,054 | B2 | 5/2017 | Lamego et al. |
| 9,697,928 | B2 | 7/2017 | Al-Ali et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,749,232 | B2 | 8/2017 | Sampath et al. |
| 9,750,442 | B2 | 9/2017 | Olsen |
| 9,750,461 | B1 | 9/2017 | Telfort |
| 9,775,545 | B2 | 10/2017 | Al-Ali et al. |
| 9,778,079 | B1 | 10/2017 | Al-Ali et al. |
| 9,782,077 | B2 | 10/2017 | Lamego et al. |
| 9,787,568 | B2 | 10/2017 | Lamego et al. |
| 9,808,188 | B1 | 11/2017 | Perea et al. |
| 9,839,379 | B2 | 12/2017 | Al-Ali et al. |
| 9,839,381 | B1 | 12/2017 | Weber et al. |
| 9,847,749 | B2 | 12/2017 | Kiani et al. |
| 9,848,800 | B1 | 12/2017 | Lee et al. |
| 9,861,298 | B2 | 1/2018 | Eckerbom et al. |
| 9,861,305 | B1 | 1/2018 | Weber et al. |
| 9,877,650 | B2 | 1/2018 | Muhsin et al. |
| 9,891,079 | B2 | 2/2018 | Dalvi |
| 9,924,897 | B1 | 3/2018 | Abdul-Hafiz |
| 9,936,917 | B2 | 4/2018 | Poeze et al. |
| 9,955,937 | B2 | 5/2018 | Telfort |

(56) References Cited

U.S. PATENT DOCUMENTS

| | | | |
|---|---|---|---|
| 9,965,946 | B2 | 5/2018 | Al-Ali et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |

(56) References Cited

U.S. PATENT DOCUMENTS

| | | | |
|---|---|---|---|
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali et al. |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Ai-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin et al. |
| D1,066,244 | S | 3/2025 | Lim et al. |
| D1,066,672 | S | 3/2025 | Al-Ali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,362,596 | B2 | 7/2025 | Barker et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,433,524 | B2 | 10/2025 | Al-Ali et al. |
| 12,440,128 | B2 | 10/2025 | Al-Ali et al. |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| D1,106,466 | S | 12/2025 | Avendaño et al. |

| | | | |
|---|---|---|---|
| 12,495,967 | B2 | 12/2025 | Muhsin et al. |
| 12,495,999 | B2 | 12/2025 | Al-Ali et al. |
| 12,507,952 | B2 | 12/2025 | Al-Ali et al. |
| 12,521,021 | B2 | 1/2026 | Al-Ali et al. |
| 12,521,506 | B2 | 1/2026 | Yu et al. |
| 12,538,084 | B1 | 1/2026 | Telfort et al. |
| 12,539,046 | B2 | 2/2026 | Kiani |
| D1,119,639 | S | 3/2026 | Al-Ali et al. |
| 12,575,797 | B2 | 3/2026 | Olsen et al. |
| D1,124,008 | S | 4/2026 | Indorf et al. |
| D1,124,017 | S | 4/2026 | Indorf et al. |
| D1,124,917 | S | 5/2026 | Al-Ali et al. |
| D1,127,209 | S | 5/2026 | Al-Ali et al. |
| 12,616,623 | B1 | 5/2026 | Al-Ali et al. |
| 12,661,488 | B2 | 6/2026 | Kiani et al. |
| 2001/0034477 | A1 | 10/2001 | Mansfield et al. |
| 2001/0039483 | A1 | 11/2001 | Brand et al. |
| 2002/0010401 | A1 | 1/2002 | Bushmakin et al. |
| 2002/0058864 | A1 | 5/2002 | Mansfield et al. |
| 2002/0133080 | A1 | 9/2002 | Apruzzese et al. |
| 2003/0013975 | A1 | 1/2003 | Kiani |
| 2003/0018243 | A1 | 1/2003 | Gerhardt et al. |
| 2003/0144582 | A1 | 7/2003 | Cohen et al. |
| 2003/0156288 | A1 | 8/2003 | Barnum et al. |
| 2003/0212312 | A1 | 11/2003 | Coffin, IV et al. |
| 2004/0106163 | A1 | 6/2004 | Workman, Jr. et al. |
| 2005/0055276 | A1 | 3/2005 | Kiani et al. |
| 2005/0234317 | A1 | 10/2005 | Kiani |
| 2006/0073719 | A1 | 4/2006 | Kiani |
| 2006/0189871 | A1 | 8/2006 | Al-Ali et al. |
| 2007/0073116 | A1 | 3/2007 | Kiani et al. |
| 2007/0180140 | A1 | 8/2007 | Welch et al. |
| 2007/0244377 | A1 | 10/2007 | Cozad et al. |
| 2008/0064965 | A1 | 3/2008 | Jay et al. |
| 2008/0094228 | A1 | 4/2008 | Welch et al. |
| 2008/0103375 | A1 | 5/2008 | Kiani |
| 2008/0221418 | A1 | 9/2008 | Al-Ali et al. |
| 2009/0036759 | A1 | 2/2009 | Ault et al. |
| 2009/0093687 | A1 | 4/2009 | Telfort et al. |
| 2009/0095926 | A1 | 4/2009 | MacNeish, III |
| 2009/0247984 | A1 | 10/2009 | Lamego et al. |
| 2009/0275844 | A1 | 11/2009 | Al-Ali |
| 2010/0004518 | A1 | 1/2010 | Vo et al. |
| 2010/0030040 | A1 | 2/2010 | Poeze et al. |
| 2010/0099964 | A1 | 4/2010 | O'Reilly et al. |
| 2010/0234718 | A1 | 9/2010 | Sampath et al. |
| 2011/0028806 | A1 | 2/2011 | Merritt et al. |
| 2011/0028809 | A1 | 2/2011 | Goodman |
| 2011/0040197 | A1 | 2/2011 | Welch et al. |
| 2011/0082711 | A1 | 4/2011 | Poeze et al. |
| 2011/0087081 | A1 | 4/2011 | Kiani et al. |
| 2011/0118561 | A1 | 5/2011 | Tari et al. |
| 2011/0137297 | A1 | 6/2011 | Kiani et al. |
| 2011/0172498 | A1 | 7/2011 | Olsen et al. |
| 2012/0123231 | A1 | 5/2012 | O'Reilly |
| 2012/0165629 | A1 | 6/2012 | Merritt et al. |
| 2012/0209084 | A1 | 8/2012 | Olsen et al. |
| 2012/0226117 | A1 | 9/2012 | Lamego et al. |
| 2012/0283524 | A1 | 11/2012 | Kiani et al. |
| 2013/0023775 | A1 | 1/2013 | Lamego et al. |
| 2013/0060147 | A1 | 3/2013 | Welch et al. |
| 2013/0096405 | A1 | 4/2013 | Garfio |
| 2013/0296672 | A1 | 11/2013 | O'Neil et al. |
| 2013/0345921 | A1 | 12/2013 | Al-Ali et al. |
| 2014/0166076 | A1 | 6/2014 | Kiani et al. |
| 2014/0180160 | A1 | 6/2014 | Brown et al. |
| 2014/0187973 | A1 | 7/2014 | Brown et al. |
| 2014/0275871 | A1 | 9/2014 | Lamego et al. |
| 2014/0275872 | A1 | 9/2014 | Merritt et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2015/0005600 | A1 | 1/2015 | Blank et al. |
| 2015/0011907 | A1 | 1/2015 | Purdon et al. |
| 2015/0073241 | A1 | 3/2015 | Lamego |
| 2015/0080754 | A1 | 3/2015 | Purdon et al. |
| 2015/0099950 | A1 | 4/2015 | Al-Ali et al. |
| 2017/0024748 | A1 | 1/2017 | Haider |

(56) References Cited

U.S. PATENT DOCUMENTS

| | | | |
|---|---|---|---|
| 2017/0251974 | A1 | 9/2017 | Shreim et al. |
| 2018/0247712 | A1 | 8/2018 | Muhsin et al. |
| 2020/0111552 | A1 | 4/2020 | Ahmed |
| 2020/0113520 | A1 | 4/2020 | Abdul-Hafiz et al. |
| 2020/0253474 | A1 | 8/2020 | Muhsin et al. |
| 2020/0253544 | A1 | 8/2020 | Belur Nagaraj et al. |
| 2020/0275841 | A1 | 9/2020 | Telfort et al. |
| 2020/0288983 | A1 | 9/2020 | Telfort et al. |
| 2020/0329993 | A1 | 10/2020 | Al-Ali et al. |
| 2021/0022628 | A1 | 1/2021 | Telfort et al. |
| 2021/0104173 | A1 | 4/2021 | Pauley et al. |
| 2021/0117525 | A1 | 4/2021 | Kiani et al. |
| 2021/0161465 | A1 | 6/2021 | Barker et al. |
| 2021/0236729 | A1 | 8/2021 | Kiani et al. |
| 2021/0275101 | A1 | 9/2021 | Vo et al. |
| 2021/0290080 | A1 | 9/2021 | Ahmed |
| 2021/0290120 | A1 | 9/2021 | Al-Ali |
| 2021/0290177 | A1 | 9/2021 | Novak, Jr. |
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0378546 | A1 | 12/2021 | Xiaojun et al. |
| 2021/0386382 | A1 | 12/2021 | Olsen et al. |
| 2022/0039707 | A1 | 2/2022 | Sharma et al. |
| 2022/0071562 | A1 | 3/2022 | Kiani |
| 2022/0096603 | A1 | 3/2022 | Kiani et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0354383 | A1 | 11/2022 | Zhunan et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Al-Ali |
| 2023/0038389 | A1 | 2/2023 | Vo |
| 2023/0045647 | A1 | 2/2023 | Vo |
| 2023/0058052 | A1 | 2/2023 | Al-Ali |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |
| 2024/0180456 | A1 | 6/2024 | Al-Ali |
| 2024/0188872 | A1 | 6/2024 | Al-Ali et al. |
| 2024/0245855 | A1 | 7/2024 | Vo et al. |
| 2024/0260894 | A1 | 8/2024 | Olsen |
| 2024/0267698 | A1 | 8/2024 | Telfort et al. |
| 2024/0277233 | A1 | 8/2024 | Al-Ali |
| 2024/0277280 | A1 | 8/2024 | Al-Ali |
| 2024/0306985 | A1 | 9/2024 | Vo et al. |
| 2024/0324953 | A1 | 10/2024 | Telfort |
| 2024/0380246 | A1 | 11/2024 | Moran |
| 2024/0380247 | A1 | 11/2024 | Moran |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |
| 2025/0100482 | A1 | 3/2025 | Al-Ali et al. |
| 2025/0118415 | A1 | 4/2025 | Olsen |
| 2025/0255764 | A1 | 8/2025 | Stead |
| 2025/0278512 | A1 | 9/2025 | Koo et al. |
| 2025/0281059 | A1 | 9/2025 | Avendano |
| 2025/0288250 | A1 | 9/2025 | Al-Ali et al. |
| 2025/0295366 | A1 | 9/2025 | Al-Ali et al. |
| 2025/0302426 | A1 | 10/2025 | Ha et al. |
| 2025/0311949 | A1 | 10/2025 | Al-Ali et al. |
| 2025/0318761 | A1 | 10/2025 | Al-Ali et al. |
| 2025/0322950 | A1 | 10/2025 | Al-Ali et al. |
| 2025/0323417 | A1 | 10/2025 | Rey |
| 2025/0329240 | A1 | 10/2025 | Kiani |
| 2025/0344010 | A1 | 11/2025 | Al-Ali et al. |
| 2026/0014333 | A1 | 1/2026 | Fernkvist et al. |
| 2026/0014334 | A1 | 1/2026 | Danwihl |
| 2026/0048198 | A1 | 2/2026 | Vo et al. |

FOREIGN PATENT DOCUMENTS

| | | |
|---|---|---|
| CN | 114 652 298 | 6/2022 |
| WO | WO 2024/187022 | 9/2024 |

OTHER PUBLICATIONS

Li et al. Highly sensitive and selective nitric oxide sensor based on biomorphic ZnO microtubes with dual-defects assistance at low temperature; ChemicalEngineeringJournal446(2022)136846 (Year: 2022).*
Translation with paragraphs CN 110522450 (Year: 2022).*
International Search Report and Written Opinion received in PCT Application No. PCT/US2024/018920 dated Jun. 17, 2024 in 13 pages.

* cited by examiner

SYSTEMS AND METHODS FOR MONITORING RESPIRATORY GASES

RELATED APPLICATIONS

Any and all applications for which a foreign or domestic priority claim is identified in the Application Data Sheet as filed with the present application are hereby incorporated by reference under 37 CFR 1.57.

This application claims the priority benefit of U.S. Provisional Patent Application No. 63/489,145 filed on Mar. 8, 2023, entitled "SYSTEMS AND METHODS FOR MONITORING RESPIRATORY GASES," which is incorporated by reference herein in its entirety.

BACKGROUND

Field of the Invention

The present disclosure relates in general to a device and a system for monitoring a concentration of volatile breathing compounds, in particular but not limited to fractional exhaled nitric oxide (FeNO) and/or exhaled carbon monoxide (eCO), in respiratory gases of patients. A device is provided by which patients can be examined for potential presence of inflammatory diseases in the lungs.

Description of the Related Art

The content and concentration of certain respiratory gases of patients (i.e., their exhaled breath) can reveal physiological information about a person, such as a potential presence of inflammatory diseases in the lungs. Several components of the respiratory gases are either produced or altered by the cells of the lungs and the respiratory tract. The physiological information that can be examined may for instance be used to diagnose pathological conditions and/or the effect of a particular treatment. Several volatile breathing compounds exist that may and/or have been shown to reveal physiological information. Two of these indicative components are nitric oxide (NO) and carbon monoxide (CO) even though many other components may convey indications of other respiratory conditions.

SUMMARY

For purposes of summarizing the disclosure and the advantages achieved over the prior art, certain objects and advantages of the disclosure are described herein. Not all such objects or advantages may be achieved in any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these implementations are intended to be within the scope of the invention herein disclosed. These and other implementations will become readily apparent to those skilled in the art from the following detailed description of the preferred implementations having reference to the attached figures.

In one embodiment, a device configured for monitoring a concentration of at least one volatile breathing compound in respiratory gases of patients can include: a patient respiratory gas interface including a mouthpiece for the patient to blow a respiratory gas into; a connector adapted to couple the patient respiratory gas interface to a gas conduit, the gas conduit leading the respiratory gas through a flow meter and a valve, wherein the flow meter configured to measure a predefined first flux level of a patient respiratory gas flux, wherein the gas conduit is configured to further lead the patient respiratory gas through an inlet into an intermediate gas storage having a winding inner volume, wherein the intermediate gas storage is open-ended via an exhaust outlet to let patient respiratory gas exhausts in excess of a volume of the intermediate gas storage out of the same in response to the flow meter sensing an expiration of the patient respiratory gas flux; and a pump configured to draw the patient respiratory gas with a predefined second flux level in a reverse direction out of a sampling gas outlet of the intermediate gas storage and into a gas sampling line, wherein exhaled concentrations of the at least one volatile breathing compound are determined by corresponding at least one volatile breathing compound detector.

In some embodiments, the pump is arranged downstream of the at least one volatile breathing detector when the patient respiratory gas flows in the reverse direction. In some embodiments, the volatile breathing compound includes at least one of fractional exhaled nitric oxide (FeNO), exhaled carbon monoxide (eCO), hydrogen ($H_2$), hydrogen sulfide, ($H_2S$) and ammonia ($NH_3$).

In some embodiments, the corresponding at least one breathing compound detector is at least one of an NO detector, a CO detector, an $H_2$ detector, a $H_2S$ detector, and an NH3 detector. In some embodiments, the flow meter includes a feedback display unit configured to display to the patient an actual exhaled patient respiratory gas flux in relation to the predefined first flux level while the patient is exhaling.

In some embodiments, the flow meter includes a differential pressure gauge. In some embodiments, the predefined first flux of respiratory gases is between 30-70 ml/s, between 40-60 ml/s, or at least 50 ml/s.

In some embodiments, the winding inner volume of the intermediate gas storage includes rounded corners. In some embodiments, the patient respiratory gas is drawn in the reverse direction through the gas sampling line with a predefined second flux level of 40-80 ml/min, of 50-70 ml/min, or of 60 ml/min.

In some embodiments, the intermediate gas storage has a patient respiratory gas intake volume of approximately 40-80 ml, approximately 55-65 ml, or approximately 60 ml. In some embodiments, the at least one volatile breathing compound detector includes an electrochemical sensor having a response rate of up to 90% of a maximum response value in approximately 30 seconds.

In some embodiments, the at least one volatile breathing compound detector is coupled to the gas sampling line via entrance and exit adapters, wherein the adapters are configured to allow a smooth and predominantly laminar flow through the entrance and the exit of a gas sensor of the at least one volatile breathing compound detector. In some embodiments, the adapters include an inlet at a center of and an outlet at a periphery of the respective sensors allowing an approximately 90-degree deflection of the gas flow into and out of the gas sensor of the at least one volatile breathing compound detector.

In some embodiments, the device is configured for spot checking the level of volatile breathing compound in the patient respiratory gas. In some embodiments, at least one component of the device is produced by means of additive manufacturing of a plastic material.

In some embodiments, the at least one component is covered with an anti-stick material. In some embodiments, the anti-stick material includes a resin.

In accordance with one embodiment, the pump is arranged downstream of the at least one volatile breathing detector when the patient respiratory gas flows in the reverse direction. This allows the pump to be situated where it is interfering the least with other components of the device, and where is reaches best possible performance.

In another embodiment, a device configured for monitoring a concentration of at least one volatile breathing compound in respiratory gases of patients can include: a patient respiratory gas interface including a mouthpiece for the patient to blow respiratory gas into; a connector adapted to couple the patient respiratory gas interface to a gas conduit, the gas conduit leading the respiratory gas through a flow meter and a valve, the flow meter configured to measure the patient respiratory gas flux, wherein the gas conduit is configured to further lead the patient respiratory gas through an inlet into an intermediate gas storage, which is open-ended via an exhaust outlet to let patient respiratory gas exhausts in excess of the intermediate gas storage volume out of the same, in response to the flow meter sensing the expiration of the patient respiratory gas flux (i.e. the discontinuation of the exhaled breath, closing the valve); and a pump configured to draw the patient respiratory gas with a predefined second flux level in the reverse direction out of a sampling gas outlet of the intermediate gas storage and into a gas sampling line, in which the exhaled concentrations of the at least one volatile breathing compound are determined by corresponding at least one volatile breathing compound detector.

In some embodiments, the volatile breathing compound includes at least one of fractional exhaled nitric oxide (FeNO), exhaled carbon monoxide (eCO), hydrogen ($H_2$), hydrogen sulfide, ($H_2S$) and ammonia ($NH_3$). In view of the above volatile breathing compounds to be measured, it is suitable that corresponding at least one breathing compound detector provided for measurement is at least one of an NO detector, a CO detector, an $H_2$ detector, a $H_2S$ detector, and an NH3 detector. Different compounds are to be used for different diagnostic purposes, and although the description has been discussing measurement of NO and CO, those are replaceable with any of the above-mentioned compounds.

In some embodiments, the flow meter comprises a feedback display unit adapted to display to the patient the actual exhaled patient respiratory gas flux in relation to the predefined first flux level while the patient is exhaling. This feedback unit assists the patient in blowing in the mouthpiece with a pressure that is suitable for the flow to remain laminar and easy to measure with sufficient accuracy for it to be used as basis for a correct diagnose.

In some embodiments, the flow meter is a differential pressure gauge. This is an inexpensive sensor that still yields very good measurement accuracy compared to many other sensors that may yield similar results at significant higher production costs.

In some embodiments, the predefined first flux of respiratory gases is between 30-70 ml/s, between 40-60 ml/s, or at least 50 ml/s. This flux is optimal from the point of view of being measurable with good accuracy and reduce the risk of mixing early portions, such as the initial part of the exhaled breath, with late portions, such as the last part of the exhaled breath of a patient's respiratory gas from a single breath.

In some embodiments, a winding inner volume of the intermediate gas storage has rounded corners. This further reduces the risk for creation of turbulent flow when gas flows around sharp corners with reasonably high pressure.

In some embodiments, the intermediate gas storage has a patient respiratory gas intake volume of approximately 40-80 ml, approximately 55-65 ml, or approximately 60 ml. This prevents the undesired and potentially contaminated early portions of the patient's exhaled breath from being measured, since exhaled gas in excess of the volume of the intermediate gas storage is allowed to exit through the exhaust outlet.

In some embodiments, the patient respiratory gas is drawn in the reverse direction through the gas sampling line with a predefined second flux level between 40-80 ml/min, between 50-70 ml/min, or at least 60 ml/min.

In some embodiments, the NO detector and/or the CO detector are electrochemical sensors having a response rate of up to 90% of the maximum response value in approximately 30 seconds. Again, an electrochemical sensor is an inexpensive sensor that still yields very good measurement accuracy compared to many other sensors that may yield similar results at significant higher production costs.

In some embodiments, the sensors of the NO detector and/or the CO detector are coupled to the gas sampling line via adapters, the adapters being adapted to allow a smooth and laminar flow through the entrances and the exits the gas respective sensors. This further increases the measurement accuracy and reduces excess blowing resistance for the patient.

In some embodiments, the adapters have an inlet at the center of and an outlet at the periphery of the respective sensors allowing an approximately 90-degree deflection of the gas flow into and out of the gas sensor. The advantage of this is the simple and relatively inexpensive construction of the gas sampling line.

In some embodiments, the device is configured for spot-checking the levels of NO and CO in the patient respiratory gas.

In some embodiments, at least one component of the device has been produced by means of additive manufacturing of a structurally strong, stiff, and sturdy plastic material, such as acrylonitrile butadiene styrene (ABS).

In another embodiment, a system for monitoring a concentration of at least one volatile breathing compound in respiratory gases of patients can include: a patient respiratory gas interface including a mouthpiece for the patient to blow a respiratory gas into; an intermediate gas storage is in fluid communication with the patient respiratory gas interface and configured to receive the respiratory gas, wherein the intermediate gas storage is open-ended via an exhaust outlet; a flow meter and a valve in fluid communication with the patient respiratory gas interface and the intermediate gas storage, wherein the flow meter is configured to measure a predefined first flux level of a patient respiratory gas flux and to let patient respiratory gas exhausts in excess of a volume of the intermediate gas storage out of the exhaust outlet in response to the flow meter sensing an expiration of the patient respiratory gas flux, the valve closing at the sensing of the expiration of the patient respiratory gas flux; and at least one volatile breathing compound detector connected to a sampling gas outlet of the intermediate gas storage and configured to determine exhaled concentrations of the at least one volatile breathing compound from a predefined second flux level of the patient respiratory gas.

In some embodiments, the system includes a pump connected to the intermediate gas storage and configured to draw the patient respiratory gas with the predefined second flux level in a reverse direction out of the sampling gas outlet of the intermediate gas storage to the at least one volatile breathing compound detector. In some embodiments, the pump is arranged downstream of the at least one volatile breathing detector when the patient respiratory gas flows in the reverse direction.

In some embodiments, the system includes a connector adapted to couple the patient respiratory gas interface to a gas conduit, wherein the gas conduit is configured to lead the patient respiratory gas through the flow meter and the valve. In some embodiments, the gas conduit further leads the patient respiratory gas through an inlet into the intermediate gas storage.

In some embodiments, the at least one volatile breathing compound includes at least one of fractional exhaled nitric oxide (FeNO), exhaled carbon monoxide (eCO), hydrogen ($H_2$), hydrogen sulfide, ($H_2S$) and ammonia ($NH_3$). In some embodiments, the corresponding at least one breathing compound detector is at least one of an NO detector, a CO detector, an $H_2$-detector, a $H_2S$-detector, and an NH3-detector.

In some embodiments, the system includes a feed-back display unit in electrical communication with the flow meter and configured to display to the patient an actual exhaled patient respiratory gas flux in relation to the predefined first flux level while the patient is exhaling. In some embodiments, the flow meter includes a differential pressure gauge.

In some embodiments, the predefined first flux of respiratory gases is between 30-70 ml/s, between 40-60 ml/s, or at least 50 ml/s. In some embodiments, the winding inner volume of the intermediate gas storage includes rounded corners.

In some embodiments, the patient respiratory gas is drawn in the reverse direction through the gas sampling line with a predefined second flux level of 40-80 ml/min, of 50-70 ml/min, or of 60 ml/min. In some embodiments, the intermediate gas storage has a patient respiratory gas intake volume of approximately 40-80 ml, approximately 55-65 ml, or approximately 60 ml.

In some embodiments, the at least one volatile breathing compound detector includes an electrochemical sensor having a response rate of up to 90% of a maximum response value in approximately 30 seconds. In some embodiments, the at least one volatile breathing compound detector is coupled to the gas sampling line via entrance and exit adapters, wherein the adapters are configured to allow a smooth and predominantly laminar flow through the entrance and the exit of a gas sensor of the at least one volatile breathing compound detector.

In some embodiments, the adapters include an inlet at a center of and an outlet at a periphery of the respective sensors allowing an approximately 90-degree deflection of the gas flow into and out of the gas sensor of the detector. In some embodiments, the system is configured for spot checking the level of volatile breathing compound in the patient respiratory gas.

In some embodiments, the at least one component of the system is produced by means of additive manufacturing of a plastic material. In some embodiments, the at least one component is covered with an anti-stick material. In some embodiments, the anti-stick material includes a resin.

In some embodiments, the intermediate gas storage includes a winding inner volume. In some embodiments, the winding inner volume of the intermediate gas storage includes rounded corners.

All of the embodiments described above are combinable with each other without departing from the intended scope of protection.

BRIEF DESCRIPTION OF THE DRAWINGS

Various implementations will be described hereinafter with reference to the accompanying drawings. These implementations are illustrated and described by example only and are not intended to limit the scope of the disclosure. In the drawings, similar elements have similar reference numerals. It is to be understood that the accompanying drawings, which are incorporated in and constitute a part of this specification, are for the purpose of illustrating concepts disclosed herein and may not be to scale.

DETAILED DESCRIPTION

Figure 1:
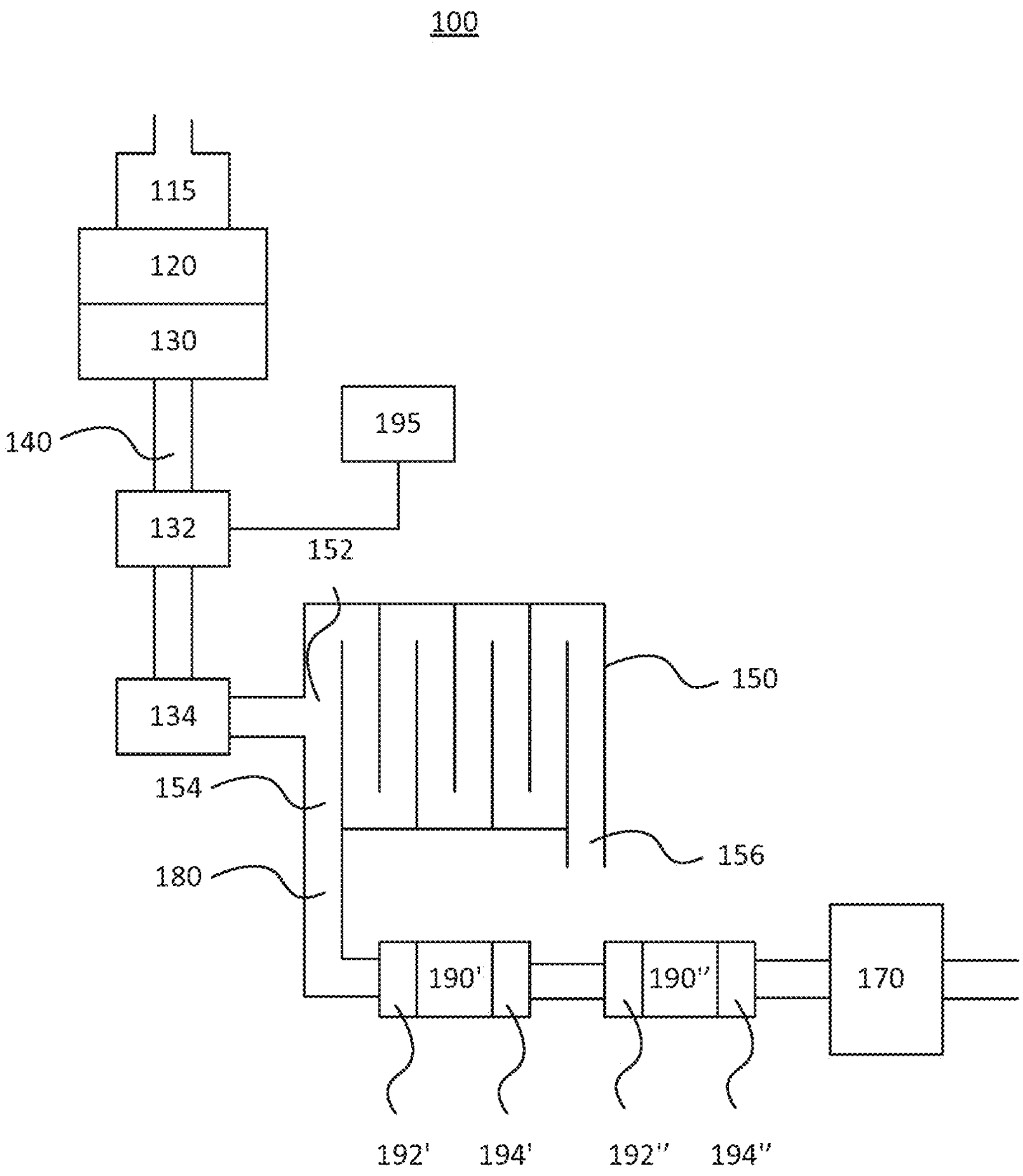
FIG. 1 is a schematic drawing of the structural features of a device for monitoring patient respiratory gas content.

The present disclosure may be understood by reference to the following detailed description. It is noted that, for purposes of illustrative clarity, certain elements in various drawings may not be drawn to scale, may be represented schematically or conceptually, or otherwise may not correspond exactly to certain physical configurations of embodiments.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments are described with reference to the accompanying figures, wherein like numerals refer to like elements throughout. The terminology used in the description presented herein is not intended to be interpreted in any limited or restrictive manner simply because it is being used in conjunction with a detailed description of some specific embodiments of the inventions. In addition, embodiments can comprise several novel features. No single feature is solely responsible for its desirable attributes or is essential to practicing the inventions herein described.

Beginning with the examination of nitric oxide, so-called fractional exhaled nitric oxide (FeNO) devices have been developed. Generally, they can be categorized as devices that relate to a novel medical technology used to aid in the diagnosis of for example asthma. FeNO devices are designed to measure fractional exhaled nitric oxide in the breath of patients. Nitric oxide (NO) is one among a plurality of volatile breathing compounds that can be used as a biomarker for asthma. Presence of NO in certain concentrations may provide an indication of the level of inflammation in the lungs of a patient. FeNO testing is typically arranged to produce a FeNO score according to a predefined scale, which gives a value to the level of inflammation and thus can be used to aid in the detection and diagnosis of asthma. Although FeNO and devices for its measurement are primarily to be seen as a diagnostic tool, it can have an additional use in the ongoing monitoring of chronic asthma.

Besides NO above, carbon monoxide (CO) is another volatile breathing compound that can exhibit properties that also make this compound suitable for use as a biomarker. CO is a ubiquitous environmental product of breathing combustion, which is also produced endogenously in the body, as a by-product of heme metabolism. CO binds to hemoglobin, resulting in decreased oxygen delivery to bodily tissues at toxicological concentrations. However, at lower concentrations (i.e., normal physiological concentrations) CO may have endogenous roles as a potential signaling mediator in vascular function and cellular homeostasis. Similar to fractional exhaled nitric oxide (FeNO), exhaled CO (eCO) has been evaluated as a promising candidate breath biomarker of pathophysiological states, including smoking status, and inflammatory diseases of the lung and other organs. As for the case of NO, which has been briefly described above, eCO values have been evaluated as potential indicators of inflammation in asthma, stable chronic obstructive pulmonary disease (COPD) and exacerbations, cystic fibrosis, lung cancer, during surgery or during critical care. The utility of eCO as a marker of inflammation, and potential diagnostic value still remains to be fully characterized. Among other volatile breathing compounds that are mentioned in the scientific literature as candidate "medicinal gases" with therapeutic potential, CO has been shown to display promising properties, acting as an effective anti-inflammatory agent in preclinical animal models of inflammatory disease, acute lung injury, sepsis, ischemia/reperfusion injury and organ graft rejection. Current and future clinical trials will further evaluate the value and clinical applicability of this gas as a suitable biomarker and/or therapeutic in human disease.

With respect to NO, it is produced in a patient's body by endothelial cells on the inner surface of blood vessels, nerve cells and inflammatory cells. In the human respiratory system, alveolar cells, the respiratory tract epithelium, or another type of cells in contact with the lungs or the airways of the respiratory tract produce endogenous NO. This NO is secreted into the air in the respiratory ducts and/or lungs of the patient. In result of a patient exhaling, the concentration of the NO content in the exhaled respiratory air can be determined.

The article "An official ATS clinical practice guideline: interpretation of exhaled nitric oxide levels (FENO) for clinical applications", R A Dweik, P B Boggs et al., Am J Respir Crit Care Med, Vol 184, pp 602-615, 2011, introduces a scientific study in which it is shown that smoking reduces FeNO. Experimentally, the value of exhaled nitric oxide is used to identify asthma in smoking patients with asthma-like symptoms. The study further concludes that FeNO cut-off levels needed to achieve high sensitivity or specificity were lower in current smokers. Therefore, it is meant that measuring the exhaled concentration of FeNO together with eCO concentration allows to determine lung inflammation and symptoms with smokers as well as healthy patients.

Hence, an evaluation of the production of endogenous NO in the lungs and respiratory ducts provides a measurement of the condition and/or function of the lungs and respiratory ducts. The accuracy of the measurement of NO in respiratory air is surprisingly good because NO measured in the respiratory air is unlikely to emanate from other organs in the body since NO produced in other locations of the body would immediately bind to the blood's hemoglobin. This would result in the NO content being broken down subsequently leaving no measurable remains.

NO is formed endogenously along the whole breathing pathway (i.e., in the oral cavity) in the sinuses, in the nose, in the trachea past the larynx, in the bronchia, and within the "free space" in the lungs, as well as in the inner blood-filled parts of the lungs. As the diagnostic purpose is directed to the condition of the lungs and/or respiratory tract, the NO generated in the volume of the mouth, nose, throat, and bronchus are of less interest and should advantageously be disregarded.

In some instances, the volume of the mouth, nose, throat, and bronchus is denoted as a so-called "dead space". An approximation made in order to quantify this volume and adapt to varying circumstances is 2 ml per kg of body weight, although certain deviations are natural to occur with regard to patients' differing physique, age, sex, and further due to the possible use of breathing aids such as tracheotomy or intubation tubing.

There can be significant advantages from a diagnostic perspective with collecting a sample for NO measurement towards the end of an exhalation of a patient's breath. As the last part of a breath is to be collected, the initial phase of the patient's breath can be discarded by allowing a volume of the patient's breath exceeding the volume of the undesired dead space to flow through the measuring device as exhaust before starting sampling of the breath.

Described herein are systems, devices, and methods for monitoring patient respiratory gas content. A device is proposed for monitoring a concentration of at least one volatile breathing compound in respiratory gases of patients, comprising a patient respiratory gas interface, comprising a mouthpiece for the patient to blow respiratory gas into, a connector adapted to couple the patient respiratory gas interface to a gas conduit, the gas conduit leading the gas through a flow meter and a valve, the flow meter being adapted to measure the patient respiratory gas flux, the gas conduit further leading the patient respiratory gas through an inlet into an intermediate gas storage, which is open-ended via an exhaust outlet to let patient respiratory gas exhausts in excess of the intermediate gas storage volume out of the same. In response to the flow meter sensing the expiration of the patient respiratory gas flux, i.e., the discontinuation of the exhaled breath, closing the valve.

Furthermore, a pump can be configured to draw the patient respiratory gas with a predefined second flux level in the reverse direction out of a sampling gas outlet of the intermediate gas storage and into a gas sampling line, in which the exhaled concentrations of the at least one volatile breathing compound are determined by corresponding at least one volatile breathing compound detector.

FIG. 1 is a schematic drawing of the structural features of a device 100 for monitoring patient respiratory gas content as mentioned above. The device 100 can include a patient respiratory gas interface 120 having a mouthpiece 115 in which the patient blows respiratory gas into. In some embodiments, the patient respiratory gas interface 120 and mouthpiece 115 can be in fluid communication with a connector 130. The device 100 can further include a flow meter 132 and a valve 134, in which the flow meter 132 being adapted to measure a predefined first flux level of a patient respiratory gas flux. The predefined first flux of respiratory gases can be between 5-100 ml, between 10-90 ml, between 20-80 ml, between 30-70 ml/s, between 40-60 ml/s, or at least 50 ml/s. In some embodiments, the flow meter 132 can comprise a differential pressure gauge. The connector 130 can be adapted to couple the patient respiratory gas interface 120 to a gas conduit 140, which leads the gas through the flow meter 132 and valve 134. The device 100 can be provided with a feedback unit 195 that measures the flow of which the patient blows into the respiratory gas interface 120 and displays to the patient the actual exhaled gas flux in relation to the predefined first flux level in real time (i.e., while the patient is exhaling). The device 100 can be configured for spot checking a level of volatile breathing compound in the patient respiratory gas.

The device 100 can include an intermediate gas storage 150 having an inner winding volume, which can be open-ended via an exhaust outlet 156 to let out patient respiratory gas exhausts in excess of a volume of the intermediate gas storage 150. The intermediate gas storage 150 can have a patient respiratory gas intake volume of approximately 10-120 ml, approximately 20-100 ml, approximately 30-90 ml, approximately 40-80 ml, approximately 55-65 ml, or approximately 60 ml. In some embodiments, the winding inner volume of the intermediate gas storage 150 can include rounded corners. In response to the flow meter 132 sensing the expiration of the patient respiratory gas flux (i.e., the discontinuation of the exhaled breath), the valve 134 can be closed. In some embodiments, the gas conduit 140 can further lead the patient respiratory gas through an inlet 152 into the volume of the intermediate gas storage 150.

At least one volatile breathing compound detector 190', 190" can be connected to a sampling gas outlet 154 of the intermediate gas storage 150 and configured to determine exhaled concentrations of the at least one volatile breathing compound from a predefined second flux level of the patient respiratory gas. In some embodiments, a pump 170 can be capable of and arranged to draw the patient respiratory gas with the predefined second flux level in the reverse direction out of the sampling gas outlet 154 of the intermediate gas storage 150 and into a gas sampling line 180. The predefined second flux level can be 10-120 ml/min, 20-100 ml/min, 40-80 ml/min, of 50-70 ml/min, and/or of 60 ml/min. This can be where the exhaled concentrations of the at least one volatile breathing compound are determined by the corresponding at least one volatile breathing compound detector 190', 190". In some embodiments, the detectors 190', 190" can include entrance and exit adapters 192', 194'; 192", 194" respectively, for coupling to the gas sampling line 180. The adapters 192', 194'; 192", 194" of the detectors 190', 190" respectively, can be constructed so as to allow a smooth and predominantly laminar flow through the entrance 192', 192" and the exit 194', 194" of the gas sensor of the detectors 190', 190". The adapters 192', 194'; 192", 194" can include an inlet at a center of and an outlet at a periphery of the respective sensors allowing an approximately 90-degree deflection of the gas flow into and out of the gas sensor of the at least one volatile breathing compound detector 190', 190". The volatile breathing compound can include at least one of fractional exhaled nitric oxide (FeNO), exhaled carbon monoxide (eCO), hydrogen ($H_2$), hydrogen sulfide, ($H_2S$) and/or ammonia ($NH_3$). In some embodiments, the at least one volatile breathing compound detector 190', 190" can include an electrochemical sensor having a response rate of up to 90% of a maximum response value in approximately 30 seconds.

The intermediate gas storage 150 can be a variety of conceivable storages, such as a maze, a labyrinth, a buffer, or a hose that has been coiled up to reduce the space taken up by the volume. It is not the shape of the storage volume as such that matters, but rather that the outer dimensions of the volume are designed to avoid bulky constructions to achieve slenderer and easier to produce shapes of the device. The size and shape of the tubular shape of the inner volume, however, can be shaped to allow for a gas flow that remains laminar under pressure to yield predictable measurement results. It can also be tubular so as to reduce the risk of mixing the initial portions of a patient's breath with the terminal portion of the same, which terminal portion is the more interesting to analyze from a diagnostic perspective. Furthermore, it can be advantageous to allow the exhalation flow from the patient to settle to a continuous flow, such that a steady level of exhaled NO is reached. The state which is sought after is known as a plateau of the exhalation.

The device 100 can be constructed so as to exert a suitable blowing resistance for the patient. With this in mind, it reflects the skilled person's choice components and of their dimensions, such as diameter of conduits, mouthpiece, gas connector inlets, and outlets of gas. For optimum function of the device 100 and associated system, is important that there is a suitable resistance for the patient to experience an overpressure in the mouth while exhaling, because that displaces nasal air which would otherwise potentially contaminate the measurement with undesired impurities, thereby reducing the likelihood of determining results that could diagnose the risk for or presence of inflammatory diseases in the lungs.

The buffered exhaled breath can be pumped out of the sampling gas outlet 154 from the intermediate gas storage 150 by means of the pump 170, which can be placed downstream of the detectors 190', 190" when the patient respiratory gas flows in the reverse direction. The pump 170 could, for example, be a membrane pump, which can make sure that there can be no backflow through the pump 170 contaminating the sample breath in the buffer chamber during the inhalation and/or exhalation phase. The pump 170 can be expunging the gases at the rate of approximately 50-250 ml/min, 100-200 ml/min, 120-180 ml/min, of 140-160 ml/min, and/or of approximately 150 ml/min. The NO and/or CO detectors can be electrochemical sensors with a relatively slow response, which can lead to the inclusion of the intermediate gas storage 150 and the pump 170. The pump 170 can flow the collected sample breath over the sensor at such a rate that the detectors 190', 190" have sufficient time to respond to the NO and/or CO content of the breath and thus being able to accurately sense inflammation in the airways indicated by the NO and/or CO content.

The relation between the volume of the intermediate gas storage 150, the second predetermined flux, and the response time of detectors 190', 190" can depend on each other. Which gas storage volumes, flow rates, and detector performance for optimum function in relation to cost is something that a skilled person will readily be able to determine and optimize based on his/her general technical ability and the easily recognizable correspondence between the relevant rates and relations already known in the technical field.

In manufacturing the device 100, at least one component of the device 100 can produced by means of additive manufacturing of a plastic material. For example, any component of the device 100 of a structurally strong, stiff, and sturdy plastic material, such as acrylonitrile butadiene styrene (ABS). Additionally, at least one component can be covered with an anti-stick material such as a resin (e.g., Teflon®).

This device can be advantageous in many ways. One of the advantages is that the undesired portion of a patient's respiratory gas contained in a breath, in the prior art also called the dead space, can be completely avoided without approximating individual deviations in lung volume or blowing capacity. Moreover, the device does not need to be adjusted individually in dependence of a patient's physique, age, sex, or to possible external factors like use of breathing aids such as tracheotomy or intubation tubing. One device can be able to serve patients equally well, without the replacement components or adjusting any settings of the device.

The inventors realized that the last portion of the breath is afflicted with fewer sources of measurement errors, and that the so-called desired plateau for optimal measurement precision is present towards the very end of each breath. Therefore, according to one embodiment, an NO detector, an CO detector and/or possibly other types of detectors will be sampling the patient respiratory gas on the last part of the exhaled gas volume, irrespective of individual deviations, hence further potentially decreasing the influence of various sources of error and therefore enhancing the accuracy and repeatability of measurements.

Yet another advantage is that by measuring the very last part of the breath, a shorter time of breath may be sufficient for obtaining an acceptable measurement result. This is of particular importance as certain patients with a more severe condition and/or experiencing physiological constraints, may find it difficult to make an exhalation for a longer period in time, i.e., for approximately ten seconds or more. However, given the construction and/or function of the device, about 5 seconds of exhalation may be sufficient. This exhalation is divided in two, of which the first half is disposed of and the rest fills the intermediate gas storage. However, for patients who are able to exhale for longer periods, the inventive device of course works just as well. The recommendation is still to obtain measurements on an exhalation over 10 seconds or longer.

Medical devices for monitoring content and/or concentrations of certain possible biomarkers in respiratory gases can be simple and robust from a constructional point of view. In some embodiments, a device is proposed in which a single valve can be sufficient in order to achieve the intended function. Prior art solutions are more complex from a constructional view, since they require at least two valves, which valves for functional reasons need to operate in synchronization with each other for comparable performance. By the device, a simpler device is achieved in which the requirement for synchronization is completely avoided, which, as a consequence, provides for a more robust device, which is less prone to dysfunction. Due to reduced complexity, it is also potentially less costly to produce than the estimated production costs of comparable devices according to the prior art.

Reversal of the flow direction can make it possible to close an already existing valve which is provided towards the patient's end of the conduit. Placing the single valve at the end of the patient even further reduces the risk for sampling gas to be contaminated by exhaled gas from the patient during the measurement phase.

Spirometry is a well-known physiological test that measures how an individual inhales or exhales volumes of air as a function of time. The primary signal measured in spirometry may be volume or flow. Physiologists describe spirometry as invaluable as a screening test of respiratory health generally in the same way that blood pressure has long provided important information about general cardiovascular health.

However, on its own, spirometry does not lead clinicians directly to an etiological diagnosis, particularly inflammatory diseases in the lungs. See further the review article Standardization of spirometry, Eur Respir J 2005, 319-338, Series "ATS/ERS Task Force: Standardisation of Lung Function Testing", V. Brusasco, R. Crapo and G. Viegi (ed.). In view of this, it is proposed that spirometry can be combined with measurements of a variety of volatile breathing compounds used for breath gas analyses, in particular using relatively slow sensors, such as electrochemical sensors.

For the sake of clarity and conciseness, it is to be mentioned that patients according to this disclosure may or may not exhibit lung inflammation or similar symptoms, such as asthma or early stages of the same. However, albeit not yet exhibiting or ever exhibiting any symptoms, as a definition of the term patients is here meant anyone who is under examination for the potential presence of inflammatory diseases in the lungs. In addition to NO and CO, which have been described above, some embodiments may also relate to monitoring of other volatile breathing compounds like $H_2$ (hydrogen), $H_2S$ (hydrogen sulfide) or NH3 (ammonia).

Figure 2:
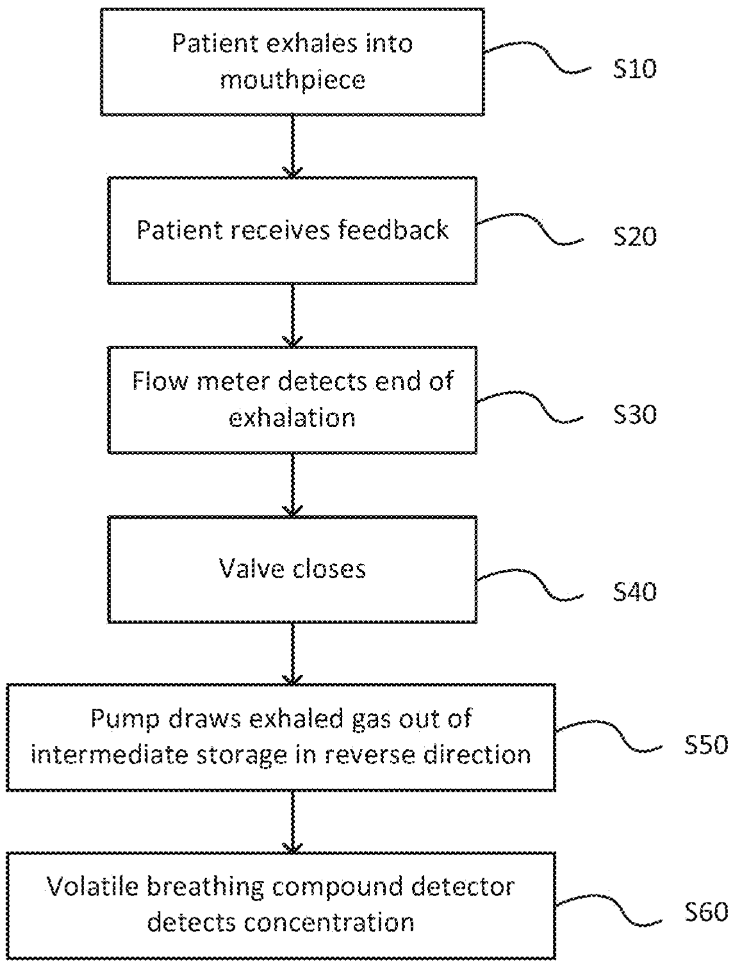
FIG. 2 is a schematic diagram of the steps of measuring patient respiratory gas content.

FIG. 2 is a schematic diagram of the steps of measuring patient respiratory gas content. The sequence begins at block S10 with a patient exhaling into the mouthpiece 115 of the patient respiratory gas interface 120 via the connector 130. According to one embodiment, at block S20, the patient can receive feedback of the actual exhaled gas flux in relation to the predefined first flux level in real time (i.e., while the patient is exhaling) from the feedback unit 195 that measures the flow of which the patient blows into the respiratory gas interface 120.

As soon as a flow meter 132 at block S30 has detected that a patient has reached the end of their actual exhalation, the valve 134 can be closed at block S40 so as to avoid any gas entering the gas conduit 140 from which the gas was lead through mouthpiece, gas interface flow meter 132, and valve 134 into the intermediate gas storage 150 via an inlet 152.

As soon as a pump 170 starts to exert its pumping energy on the gas content in the intermediate gas storage 150, pump 170 at block S50 can draw exhaled gas out of intermediate storage 150 in the reverse direction and through an outlet 154 to a gas sampling line 180. Then at block S60, the gas passes detectors 190', 190" by which at least one volatile breathing compound is determined.

Figure 3A:
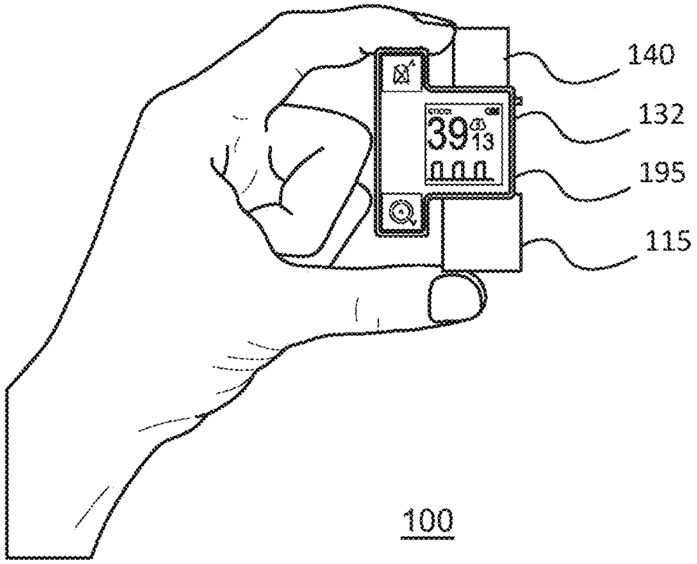
FIGS. 3A and 3B illustrate a portion of an example embodiment of the device 100.
Figure 3B:
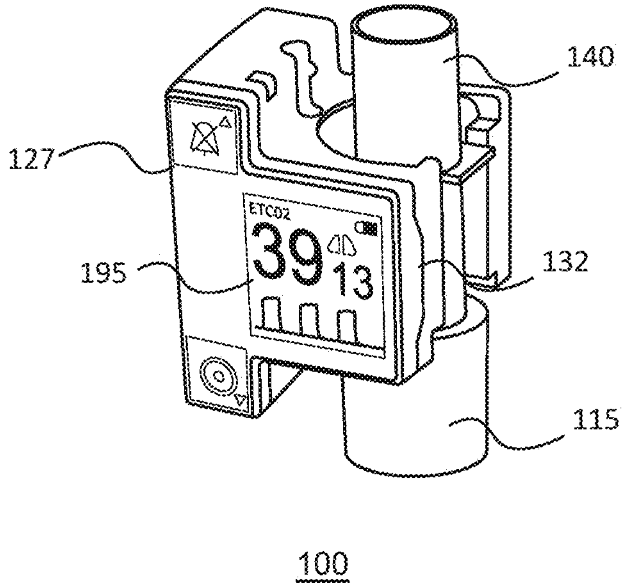

FIGS. 3A and 3B illustrate a portion of an example embodiment of the device 100. The device 100 as illustrated demonstrates the mouthpiece 115, flow meter 132, feedback unit 195, and gas conduit 140. The flow meter 132 can include electronic circuitry for processing the signals generated by the flow of the predefined first flux level while the patient is exhaling and the feedback unit 195 for displaying the measurement results (e.g., flow rate, start and stop of flow, and the like) and a control panel 127 can allow the user to adjust and/or select measurement parameters. In some examples, the display 195 can be a touchscreen display that may allow the user to adjust and/or select measurement parameters.

Figure 4:
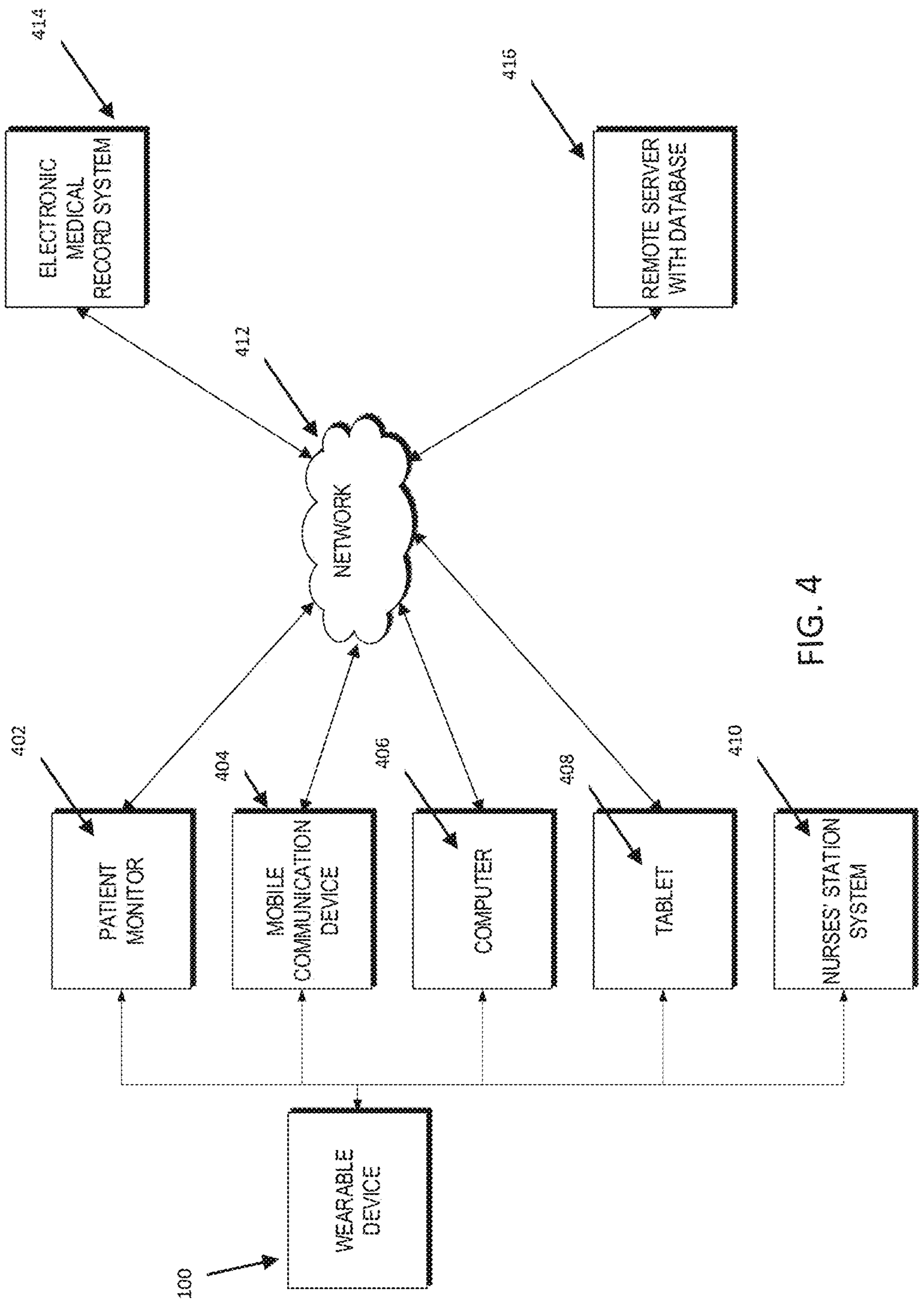
FIG. 4 is a diagram illustrating schematically a network of non-limiting examples of devices that can communicate with the device disclosed herein.

The device 100 can be used in a standalone manner and/or in combination with other devices and/or sensors. In some embodiments, as shown in FIG. 4 the device 100 can connect (for example, wirelessly) with a plurality of devices, including but not limited to a patient monitor 402 (for example, a bedside monitor such as Masimo's Radical-7®, Rad-97® (optionally with noninvasive blood pressure or NomoLine capnography), and Rad-8® bedside monitors, a patient monitoring and connectivity hub such as Masimo's Root® Platform, any handheld patient monitoring devices, and any other wearable patient monitoring devices), a mobile communication device 404 (for example, a smartphone), a computer 406 (which can be a laptop or a desktop), a tablet 408, a nurses' station system 410, glasses such as smart glasses configured to display images on a surface of the glasses and/or the like. The wireless connection can be based on Bluetooth technology, near-field communication (NFC) technology, and/or the like. Additionally, the device 100 can connect to a computing network 412 (for example, via any of the connected devices disclosed herein, or directly). The network 412 may comprise a local area network (LAN), a personal area network (PAN) a metropolitan area network (MAN), a wide area network (WAN) or the like, and may allow geographically dispersed devices, systems, databases, servers (e.g., cloud-based), and the like to connect (e.g., wirelessly) and to communicate (e.g., transfer data) with each other. The device 100 can establish connection via the network 412 to one or more electronic medical record system 414, a remote server with a database 416, and/or the like.

Optionally, the device 100 can be integrated with more sensors and/or configured to connect to a plurality of external sensors, wirelessly or with a connecting cable. The connecting cable can be a universal connector configured to connect to any of the medical devices and/or sensors disclosed herein to provide communication between the device 100 and the connected medical devices and/or sensors. The cable can optionally include a board-in-cable device that includes its own processor, but may not include its own display.

Unless the context clearly requires otherwise, throughout the description and the claims, the words "comprise," "comprising," "include," "including" and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Likewise, the word "connected", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Moreover, as used herein, when a first element is described as being "on" or "over" a second element, the first element may be directly on or over the second element, such that the first and second elements directly contact, or the first element may be indirectly on or over the second element such that one or more elements intervene between the first and second elements. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments.

Several illustrative examples of systems and methods for monitoring respiratory gases have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps may be arranged or performed differently than described and components, elements, features, acts, or steps may be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations may also be implemented in combination in a single implementation. Conversely, various features that are described in the context of a single implementation also may be implemented in multiple implementations separately or in any suitable subcombination. Moreover, although features may be described above as acting in certain combinations, one or more features from a claimed combination may in some cases be excised from the combination, and the combination may be claimed as a subcombination or variation of a subcombination.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures may or may not be drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components may be added, removed, and/or rearranged. Further, the disclosure herein of any particular feature, aspect, method, property, characteristic, quality, attribute, element, or the like in connection with various examples may be used in all other examples set forth herein. Additionally, any methods described herein may be practiced using any device suitable for performing the recited steps.

For purposes of summarizing the disclosure, certain aspects, advantages, and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures, or description herein. For example, various functionalities provided by the illustrated modules may be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification may be included in any example.

What is claimed is:

1. A device configured for monitoring a concentration of at least one volatile breathing compound in respiratory gases of patients, the device comprising:

a patient respiratory gas interface comprising a mouthpiece for the patient to blow a respiratory gas into;

a connector adapted to couple the patient respiratory gas interface to a gas conduit, the gas conduit leading the respiratory gas through a flow meter and a valve, wherein the flow meter is configured to measure a predefined first flux level of a patient respiratory gas flux, wherein the gas conduit is configured to further lead the patient respiratory gas through an inlet into an intermediate gas storage having a winding inner volume, wherein the intermediate gas storage is open-ended via an exhaust outlet to let patient respiratory gas exhausts in excess of a volume of the intermediate gas storage out of the same in response to the flow meter sensing an expiration of the patient respiratory gas flux; and a pump configured to draw the patient respiratory gas with a predefined second flux level in a reverse direction, wherein the reverse direction is opposite to a direction in which the patient respiratory gas flows from the mouthpiece into the intermediate gas storage, out of a sampling gas outlet of the intermediate gas storage and into a gas sampling line, wherein exhaled concentrations of the at least one volatile breathing compound are determined by corresponding at least one volatile breathing compound detector.

2. The device of claim 1, wherein the pump is arranged downstream of the at least one volatile breathing compound detector when the patient respiratory gas flows in the reverse direction.

3. The device of claim 1, wherein the volatile breathing compound includes at least one of fractional exhaled nitric oxide (FeNO), exhaled carbon monoxide (eCO), hydrogen ($H_2$), hydrogen sulfide ($H_2S$), and ammonia ($NH_3$).

4. The device of claim 1, wherein the corresponding at least one volatile breathing compound detector is at least one of an NO detector, a CO detector, an $H_2$ detector, a $H_2S$ detector, and an $NH_3$ detector.

5. The device of claim 1, wherein the flow meter comprises a feedback display unit configured to display to the patient an actual exhaled patient respiratory gas flux in relation to the predefined first flux level while the patient is exhaling.

6. The device of claim 1, wherein the predefined first flux level of the patient respiratory gas flux is between 30-70 ml/s.

7. The device of claim 1, wherein the patient respiratory gas is drawn in the reverse direction through the gas sampling line with a predefined second flux level of 40-80 ml/min.

8. The device of claim 1, wherein the intermediate gas storage has a patient respiratory gas intake volume of approximately 40-80 ml.

9. The device of claim 1, wherein the at least one volatile breathing compound detector is coupled to the gas sampling line via entrance and exit adapters, wherein the adapters are configured to allow a smooth and predominantly laminar flow through the entrance and the exit of a gas sensor of the at least one volatile breathing compound detector.

10. A system for monitoring a concentration of at least one volatile breathing compound in respiratory gases of patients, the system comprising:

a patient respiratory gas interface comprising a mouthpiece for the patient to blow a respiratory gas into;

an intermediate gas storage in fluid communication with the patient respiratory gas interface and configured to receive the respiratory gas, wherein the intermediate gas storage is open-ended via an exhaust outlet to let patient respiratory gas exhausts in excess of a volume of the intermediate gas storage out of the exhaust outlet;

a flow meter and a valve in fluid communication with the patient respiratory gas interface and the intermediate gas storage, wherein the flow meter is configured to measure a predefined first flux level of a patient respiratory gas flux and to let patient respiratory gas exhausts in excess of a volume of the intermediate gas storage out of the exhaust outlet in response to the flow meter sensing an expiration of the patient respiratory gas flux, the valve closing at the sensing of the expiration of the patient respiratory gas flux; and at least one volatile breathing compound detector connected to a sampling gas outlet of the intermediate gas storage and configured to determine exhaled concentrations of the at least one volatile breathing compound from a predefined second flux level of the patient respiratory gas.

11. The system of claim 10, further comprising a pump connected to the intermediate gas storage and configured to draw the patient respiratory gas with the predefined second flux level in a reverse direction, wherein the reverse direction is opposite to a direction in which the patient respiratory gas flows from the mouthpiece into the intermediate gas storage, out of the sampling gas outlet of the intermediate gas storage to the at least one volatile breathing compound detector.

12. The system of claim 11, wherein the pump is arranged downstream of the at least one volatile breathing compound detector when the patient respiratory gas flows in the reverse direction.

13. The system of claim 10, wherein the at least one volatile breathing compound includes at least one of fractional exhaled nitric oxide (FeNO), exhaled carbon monoxide (eCO), hydrogen ($H_2$), hydrogen sulfide ($H_2S$), and ammonia ($NH_3$).

14. The system of claim 10, wherein the at least one volatile breathing compound detector is at least one of an NO detector, a CO detector, an $H_2$ detector, a $H_2S$ detector, and an $NH_3$ detector.

15. The system of claim 10, further comprising a feedback display unit in electrical communication with the flow meter and configured to display to the patient an actual exhaled patient respiratory gas flux in relation to the predefined first flux level while the patient is exhaling.

16. The system of claim 10, wherein the predefined first flux level of the patient respiratory gas flux is between 30-70 ml/s.

17. The system of claim 10, wherein the patient respiratory gas is drawn in a reverse direction through a gas sampling line with a predefined second flux level of 40-80 ml/min.

18. The system of claim 10, wherein the intermediate gas storage has a patient respiratory gas intake volume of approximately 40-80 ml.

19. The system of claim 10, wherein the at least one volatile breathing compound detector comprises an electrochemical sensor having a response rate of up to 90% of a maximum response value in approximately 30 seconds.

20. The system of claim 10, wherein the at least one volatile breathing compound detector is coupled to a gas sampling line via entrance and exit adapters, wherein the adapters are configured to allow a smooth and predominantly laminar flow through the entrance and the exit of a gas sensor of the at least one volatile breathing compound detector.

* * * * *